United States Patent [19]

Yukl

[11] 4,318,108
[45] Mar. 2, 1982

[54] BIDIRECTIONALLY FOCUSING ANTENNA

[75] Inventor: Tex N. Yukl, Banks, Oreg.

[73] Assignee: Near Field Technology Co., Portland, Oreg.

[21] Appl. No.: 970,378

[22] Filed: Dec. 18, 1978

Related U.S. Application Data

[63] Continuation of Ser. No. 792,527, May 2, 1977, abandoned.

[51] Int. Cl.³ .................. H01Q 15/00; G01R 27/04
[52] U.S. Cl. ................................. 343/753; 343/908; 324/58.5 A
[58] Field of Search ............ 343/908, 741, 742, 743, 343/753, 754; 250/341; 324/58.5 A, 58.5 B, 58.5 C, 58A, 58 B

[56] References Cited

U.S. PATENT DOCUMENTS

| | | | |
|---|---|---|---|
| 2,576,181 | 11/1951 | Iams | 343/754 |
| 2,795,783 | 6/1957 | Dunbar | 343/754 |
| 3,233,172 | 2/1966 | Luoma | 324/58 B |
| 3,491,361 | 1/1970 | Campbell | 343/741 |

*Primary Examiner*—Eli Lieberman
*Attorney, Agent, or Firm*—Kolisch, Hartwell & Dickinson

[57] ABSTRACT

A transmission/reception antenna for electromagnetic energy of a selected wavelength. The antenna features a central radiation-effective expanse which, in the case of transmission, functions as a driven element, and in the case of reception, functions as a main receiving element. Cooperating with this expanse is a focusing lens which produces simultaneously on opposite sides of the antenna a pair of symmetrically spaced focal points relative to the expanse—such points being separated by a distance substantially equaling one-half the mentioned selected wavelength.

28 Claims, 3 Drawing Figures

BIDIRECTIONALLY FOCUSING ANTENNA

CROSS-REFERENCE TO RELATED APPLICATION

This is a continuation of my prior-filed copending application entitled "Bidirectionally Focusing Antenna", Ser. No. 792,527, filed May 2, 1977, now abandoned.

BACKGROUND AND SUMMARY OF THE INVENTION

This invention pertains to an antenna for electromagnetic energy, and more particularly to such an antenna which is bidirectionally focused.

I have discovered that the phenomenon of standing waves in an electromagnetic transmission medium can be used advantageously in investigating various internal conditions in different substances. For example, this phenomenon can be used to monitor physiological conditions within different parts of a person's body, and can also be used, as a further illustration, in an application such as flaw detection in metals. More specifically, by directing electromagnetic radiation of a known wavelength toward what might be thought of as an interrogation zone inside a substance, and through locating this zone at, for example, a distance of substantially one-quarter of the wavelength of the radiation from the central radiating element in an antenna, measurements may be made at another point along the transmission axis of the antenna which will provide a direct indication of electrical characteristics, such as impedance, within the interrogated zone.

A general object of the present invention is to provide a unique antenna for bidirectionally radiating energy so as to take full advantage of this standing-wave measurement possibility.

More specifically, an object of the invention is to provide such an antenna which operates in a bidirectional manner with respect to a central element in the antenna.

Still another object of the invention is to provide such an antenna which is constructed in a special manner so as to focus radiation bidirectionally at a pair of spaced-apart focal points that are disposed symmetrically with respect to the antenna, and are spaced by a distance substantially equaling one-half the wavelength of the radiation intended for the antenna.

A preferred embodiment of the proposed antenna features a central, generally ring-like radiation-effective expanse, which has a nominal circumference equaling the wavelength of the radiation planned for the antenna. Fitted symmetrically with respect to this expanse is a specially shaped lens which produces a pair of symmetrically spaced focal points relative to the expanse—such points being separated by the half-wavelength distance mentioned above.

The expanse just mentioned, which is also referred to as the driven expanse in the antenna, is driven at a pair of diametrically opposed points, with signals fed to these points being substantially exactly 180° out-of-phase. As a consequence of this arrangement, radiation actually occurs from a pair of points on the expanse disposed in quadrature with respect to the driving connection just mentioned. The fact radiation occurs from points is a feature which greatly enhances the overall resolution obtainable at the focal points of the antenna. Radiation emanating from the two radiation points is directed in opposite directions along what might be thought of as the transmission axis of the antenna toward the antenna's focal points. The fact that two points of radiation are employed, which points are spaced apart, greatly facilitates focusing of radiated energy at the focal points.

When the antenna is used, it is contemplated that it will be adjusted so as to place one of its two focal points adjacent a selected interrogation zone. The size of the interrogation zone is determined, essentially, through the size of a conductive receiver, which is used along with the antenna, and is located adjacent the other focal point. A form of receiver which is shown herein, and which has been found to be extremely effective, is a short section of conductive tubing, whose cross-sectional area and whose axial length define the volume of the interrogation zone. Preferably, a relatively small receiving tube is used, and this is placed somewhat toward the antenna from the adjacent focal point. The receiver is not placed exactly at the location of the focal point inasmuch as, in order to be effective there, it would have to have infinitesimally small dimensions.

As will become apparent, in order to obtain maximum resolution, maximum accuracy, and maximum versatility in the antenna, there are a number of important dimensional and shape characteristics which will be mentioned below. Further, it should be noted that while the antenna is specifically described herein in connection with an operation wherein it functions primarily as a transmitting antenna, the same construction could be used as primarily a receiving antenna which has highly focused directional receiving capabilities.

Through achieving precise high-resolution focusing in a bidirectional manner, the antenna of the invention greatly facilitates the unique kind of internal investigation technique mentioned above. With the antenna in use, and with one of its focal points directed toward a zone for interrogation within a body, it is a simple matter to monitor electrical conditions of energy received by the receiving tube, and to interpret these conditions as an indication of electrical characteristics within the monitored zone. These characteristics, in turn, are interpretable to indicate various physical conditions existent in the interrogated zone.

These and other objects and advantages which are attained by the invention will become more fully apparent as the description which now follows is read in conjunction with the accompanying drawings.

DETAILED DESCRIPTION OF THE INVENTION

Figure 1:
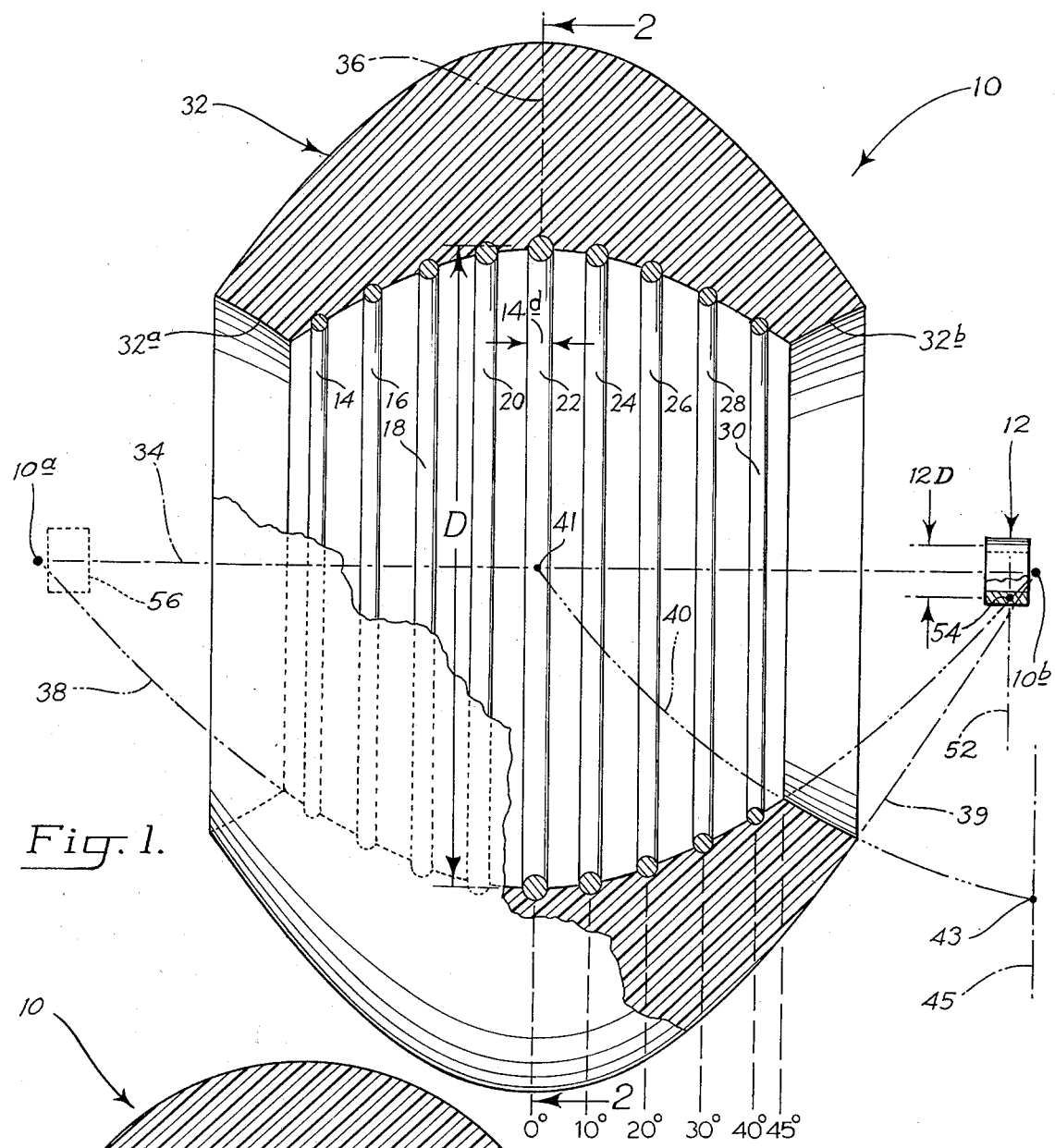
FIG. 1 is a side elevation, partly in cross section, illustrating an antenna constructed in accordance with the present invention, and also illustrating a receiver which is used in cooperation with the antenna in a specific application thereof which is described herein.
Figure 2:
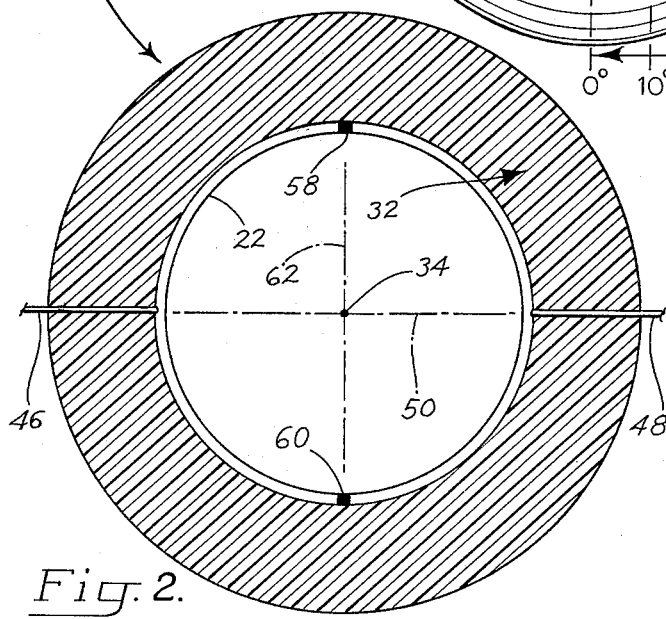
FIG. 2 is a reduced-scale cross-sectional view, taken generally along the line 2—2 in FIG. 1.

Turning now to the drawings, and considering first FIGS. 1 and 2, indicated generally at 10 is an antenna constructed in accordance with the present invention. Cooperating with antena 10, in connection with a particular application therefor which will be generally described herein, is an element 12 which is referred to as a receiver. Antenna 10 is suitably mounted for movement to different positions and attitudes, such mounting mechanism being omitted from the drawings inasmuch as it forms no part of the invention. Further, receiver 12 herein is suitably anchored in a fixed position relative to the antenna (that position in which it is illustrated in FIG. 1) by means which have also been omitted from the drawings, both because such forms no part of the present invention and also in the interest of simplification.

In general terms, antenna 10 comprises a plurality of conductive, continuous circular rings, shown at 14, 16, 18, 20, 22, 24, 26, 28, 30, which are mounted within a generally donut-shaped housing 32 that functions as a focusing lens, or means, in the antenna.

All of the rings in the antenna are substantially planar, and continuous or unbroken. The rings are formed of a solid copper wire having a circular cross section. These rings are disposed with their planes substantially parallel to one another, and perpendicular to the transmission axis 34 for the antenna. The planes containing these rings are equally spaced in a manner which will be described shortly. Ring 22 is the largest among the rings, and occupies what might be referred to as the central plane 36 of the antenna. This ring is referred to as a driven element in the antenna, and also as a means defining a driven expanse. Ring 22 also constitutes a means defining a pair of spaced radiation-effective points in the antenna, which points will be discussed more fully later.

The other rings in the antenna are referred to as director rings, or director means. It is believed obvious from a study of FIG. 1 that, advancing in both directions away from plane 36, the director rings become progressively smaller. Thus, rings 20, 24 are somewhat smaller than ring 22, but are equal in size to each other. Rings 18, 26 are smaller than rings 20, 24, and also are of equal size. Likewise, rings 16, 28 and rings 14, 30 are progressively smaller, with rings 16, 28 being of equal size, and the same also being true of rings 14, 30.

Although many different specific operating frequencies may be chosen for an antenna constructed in accordance with the invention, antenna 10 herein is constructed to work with electromagnetic radiation at a frequency of around 505 megahertz. Such a frequency has a wavelength of about 23.5 inches. For a reason which will be explained, it is desirable that the nominal circumference of driven ring 22 be substantially exactly equal to the wavelength of the selected frequency. Hence, the nominal circumference of ring 22, i.e. that circumference measured about a circular line within the body of the ring centrally between the inside and outside diameters of the ring, is about 23.5 inches.

With the nominal circumference of ring 22 thus defined, the nominal diameter of the ring, shown as dimension D in the figure, is also determined.

As was mentioned earlier, the cross-sectional area of the solid wire making up each ring is circular. Referring again specifically to ring 22, the diameter of this cross-sectional area is shown at d. With the nominal diameter of the overall ring determined as just indicated, the dimension d is determined in accordance with the following formula:

$$Z = 276(\log 2D/d)$$

Where Z equals the characteristic impedance of the antenna, D is the nominal diameter of a ring, such as ring 22, and d is the diameter of the cross-sectional area of the ring material, such as dimension d in FIG. 1.

In order to obtain maximum effectiveness in a system utilizing antenna 10, it is desirable that the characteristic impedance of the antenna be as closely matched as possible to that of the medium into which the antenna is to transmit radiation. For example, and in the case of the antenna's being used as a means for following electrical characteristics inside a person's body, it is desirable that the characteristic impedance in the antenna be closely matched to the mean impedance expected to be encountered in such a space. Antenna 10 has been so constructed, and to this end, experiments have shown that the mean impedance of tissue in a human body is around 487 ohms. Accordingly, this figure has been chosen to define the characteristic impedance of antenna 10.

From the above formula, dimension d is immediately calculatable, and turns out to be about 0.25 inches.

Turning for a moment to the construction of lens 32, the purpose of this lens in the antenna is to create a pair of spaced focal points therefor, distributed symmetrically with respect to ring 22 on transmission axis 34. More specifically, lens 32 functions to create focal points 10a, 10b on axis 34, which points are each spaced along the axis substantially exactly one-quarter of the wavelength of the frequency mentioned above from plane 36. A material for lens 32 which functions adequately for this purpose is polystyrene, and such material is used in lens 32.

A first important consideration for lens 32 is that it have an inside surface of revolution which, where it intersects a radial plane containing axis 34, curves along a substantially sinusoidal path that has a peak at the location of the nominal circumference location of ring 22, and which intersects axis 34 at focal points 10a, 10b. Such a path is illustrated in dash-double-dot lines at 38 in FIG. 1. It is obvious from this requirement that the inside wall of the lens is suitably grooved so as to receive ring 22 to the depth indicated in FIG. 1. Further, it is desirable that the path thus followed by the inside surface of lens 32 terminate at what might be thought of as the 45° point on opposite sides of plane 36. Such an angular measurement, of course, relates to the angular condition of the sinusoidal course followed by path 38 relative to plane 36. This situation is illustrated in FIG. 1 along the degree-graph-axis presented in the figure.

A further consideration of lens construction is that the radial thickness of the lens, i.e. the radial dimension of the lens, measured from its inside surface to its outside surface in different axially displaced planes which intersect axis 34 at a right angle, be a predetermined fixed percentage of the inside circumference of the lens in each such plane. More specifically, it will be noted that at the location of ring 22, where the nominal circumference of this ring coincides with path 38, such circumference is equal to the wavelength of the frequency of the antenna. The radial dimension of lens 32 in this plane, measured outwardly from the nominal circumference of ring 22, is preferably about one-tenth of this nominal circumference. This same relationship remains, progressing in axially opposite directions away from plane 36. Consequently, the outside surface of lens 32, where it intersects a radial plane containing axis 34, also follows a sinusoidal path 39, different from the first-mentioned sinusoidal path, which has a peak where it intersects plane 36, and which extends through focal points 10a, 10b. This kind of construction assures maximum efficiency in the lens.

Still another consideration of lens construction is that, at axially opposite ends thereof, the lens includes what are referred to as exit faces 32a, 32b, which face toward focal points 10a, 10b, respectively. Each of these exit faces, where it intersects a radial plane containing axis 34, curves along yet another sinusoidal path, similar to the first-mentioned sinusoidal paths, such as the path shown in dash-triple-dot lines at 40 in FIG. 1 for face 32b. Path 40 intersects axis 34 at 41 in the plane of ring 22, and has a "peak" 43 relative axis 34 where it intersects a plane 45 containing focal point 10b and normal to axis 34. The extremities of faces 32a, 32b are defined by the intersections of paths 38, 39, 40.

In order to inhibit radiation leakage through the wall of the lens, the outside surface is coated with a suitable thin conductive layer, such as a suitable silver layer. This layer is referred to herein also as electromagnetic-/electrostatic shield means.

As was mentioned earlier, director means in antenna 10 takes the form herein of a plurality of axially spaced director rings disposed on opposite sides of driven ring 22. As a matter of convenience, four such rings are used on each side of ring 22, and are spaced from each other, and from ring 22, by what might be thought of as 10° distances along the sinusoidal path of the inside surface of lens 32. This situation is illustrated by the intersections depicted for the planes of rings 24, 26, 28, 30 and the graph-degree-axis shown in FIG. 1. Each of the director rings has its nominal circumference defined by the circular path of intersection of the plane of the ring and the surface of revolution defining the inside surface of the lens. Hence, for each such ring the "D" dimension thereof is thus defined. The diameter of the cross-sectional area of the ring material for each such ring is determined, then, in accordance with the above given formula, wherein the characteristic impedance remains the same as that described earlier. As a consequence of this situation, not only do the nominal circumferences of the director rings, progressing away from ring 22, become smaller, but also the diameters of the cross-sectional areas of the rings become smaller. By way of illustration, Table I below sets forth some actual dimensions which have been used satisfactorily for the rings in antenna 10.

TABLE I

| Ring(s) | D (inches) | d (inches) |
|---------|------------|------------|
| 22      | 7.44       | 0.255      |
| 20,24   | 7.339      | 0.251      |
| 18,26   | 6.995      | 0.239      |
| 16,28   | 6.446      | 0.221      |
| 14,30   | 5.702      | 0.195      |

When antenna 10 is operated as a transmitting antenna, ring 22 therein is driven by a suitable voltage source operating at the frequency mentioned above. In order for transmission to occur best in accordance with the present invention, it is important that this ring be driven at precisely diametrically opposed points on the ring. Referring especially to FIG. 2, conductors 46, 48 are provided which extend coaxially in a plane 50 (which is at a right angle relative to the plane of the figure), normal to axis 34, and connect with such diametrically opposed points on ring 22. These conductors may take any suitable form, and may be mounted in the wall of lens 32 in any suitable manner. With such connections made, plane 50 is referred to as the high-impedance plane in the antenna. Still a further consideration with respect to operating antenna 10, it is important that connections extending between conductors 46, 48 and a source of voltage be sized to assure that signals fed to the diametrically opposed points of connection between ring 22 and conductors 46, 48 be substantially exactly 180° out of phase. Such connections form no part of the present invention, but are mentioned herein because they are important to assuring maximum efficient operation from the antenna. Those skilled in the art are well aware of how to achieve such connections.

Lens 32 has been described so far as a unitary object. In other words, it is preferable that the lens take the form of a single integrated piece of material. However, it may be simpler in some instances to form the lens in a pair of halves which are joined together. Where this kind of construction is used, it is important, again to assure maximum efficient operation of the antenna, that the separation between the halves lie in high-impedance plane 50.

As was mentioned earlier, receiver 12, in essence, defines the interrogation zone for the antenna. The purpose of the receiver is to respond to, or pick up, radiation directed by the antenna toward focal point 10b. Preferably, and as is the case in the construction shown herein, receiver 12 is located somewhat toward antenna 10 from focal point 10b. The receiver takes the form of a short length of conductive tubing. More specifically, the tube forming receiver 12 has an axial dimension, measured along axis 34, of about one-half inch, and a nominal diameter, indicated at 12D, also of about one-half inch. The wall thickness of the tube forming the receiver is about one-eighth of an inch. Receiver 12 is mounted coaxial with the antenna, and in any suitable fashion locking it into the position shown in FIG. 1 relative to the antenna. Preferably, the receiver is located relative to focal point 10b in such a manner that what might be thought of as its central axial plane 52, which is normal to axis 34, intersects path 38, where the latter intersects the nominal diameter of the receiver. This point of mutual intersection is indicated at 54 in FIG. 1.

The interrogation zone defined for antenna 10 is indicated by dashed block 56 in FIG. 1. Zone 56 is generally cylindrical, has substantially the same outside dimensions as receiver 12, and is located in what might be thought of as a mirror-image position on the opposite side of the antenna from receiver 12, slightly inwardly from focal point 10a.

When antenna 10 is used, for example to monitor a condition within a person's heart, the antenna is oriented so as to place zone 56 at the location within the heart wherein observation is desired. Electromagnetic energy from a voltage source is supplied to driven ring 22 as previously mentioned. With such energy supplied, radiation takes place in axially opposite directions from ring 22 from a pair of diametrically opposed points (indicated as darkened regions 58, 60 in FIG. 2) which are in quadrature with the points of connection between ring 22 and conductors 46, 48. These two points lie in a common plane 62 which contains axis 34 and which is normal to the plane of FIG. 2. Radiation from these two points is focused by lens 32 toward focal points 10a, 10b. The fact that radiation takes place from point locations facilitates high resolution for the lens. The director rings function along with the lens to guide radiation toward points 10a, 10b.

With the focal points of the antenna located at quarter-wavelength distances from the plane of ring 22, voltage and current conditions which exist in zone 56, as a result of the impedance of material within this zone, produce related voltage and current conditions at receiver 12. It is thus possible, through monitoring electrical conditions at the receiver, to determine certain characteristics of the material within zone 56. Connections for picking up a signal from receiver 12 are similar in nature to the driving connections made with ring 22. More specifically, these connections are preferably made in high-impedance plane 50, and with attention paid to the relative lengths of such connections so as to assure that signals received by the receiver are transmitted to monitoring apparatus with a 180° phase relationship.

The antenna thus performs to direct energy accurately into a prescribed interrogation zone, wherein electrical characteristics may be followed through electrical changes that occur in another zone (i.e. that occupied by receiver 12) to which the antenna also directs radiation. No physical contact is required with material in the interrogation zone. The location of the interrogated zone may be shifted simply by adjusting the position and attitude of the antenna. The size of the zone may be adjusted through changing the size of receiver 12.

Figure 3:
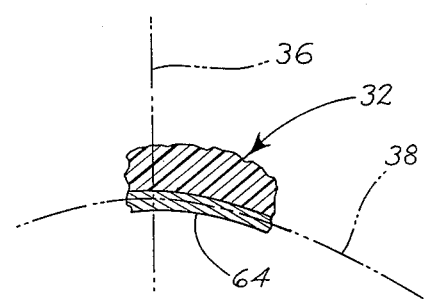
FIG. 3 is a fragmentary view from the same perspective as FIG. 1, and on about the same scale, showing a modification of the invention.

FIG. 3 of the drawings illustrates, fragmentarily, a modification of antenna 10. What is shown in this figure is a small portion of the antenna around the region where plane 36 and path 38 intersect (near the top of the antenna as shown in FIG. 1). In this modification of the invention, the driven element, or expanse, in the antenna is coextensive, and unitary, with the director means, or elements, in the antenna—in the form of a continuous conductive element mounted against the inside surface of lens 32. This element is designated 64 in FIG. 3. The radial thickness of element 64, in plane 36, is the same as dimension d for ring 22. Similarly, the thickness of the element at the locations of the planes of the director rings described above is the same in these planes as the respective cross-sectional diameter dimensions of the respective director rings. The inside and outside surfaces of element 64 follow sinusoidal paths defined by these changing dimensions. Thus, the thickness of element 64 changes from its thickest dimension in plane 36 to its thinnest dimensions at the opposite ends of the antenna. The radial center point of the wall of element 64, at all points, follows previously mentioned path 38. The outside dimensions and shape of lens 32 are identical to those of the lens shown in FIG. 1.

This modification of the invention provides a slightly higher degree of efficiency over that described in connection with FIGS. 1 and 2. A driving connection for element 64 is made in exactly the same manner as a driving connection for ring 22—namely, through diametrically opposed conductors, such as conductors 46, 48, which contact the element normal to axis 34 and within plane 50. With such connections, and with a driving signal supplied to the element, radiation takes place from a pair of spaced points within the element which correspond in location to previously mentioned points 58, 60.

While a preferred embodiment of the invention has been described herein, and several modifications suggested, it is appreciated that other variations and modifications may be made without departing from the spirit of the invention.

It is claimed and desired to secure by Letters Patent:

1. A bidirectional focusing antenna for radiating electromagnetic energy of a selected wavelength simultaneously in opposite directions along the antenna's axis, said antenna comprising
means defining a central, generally planar endless-ring-type conductive expanse having a nominal circumference substantially equaling said selected wavelength, with the plane of said expanse defining the central plane of the antenna, and being disposed normal to said axis, and
bidirectional focusing means, including electromagnetic/electrostatic shield means in the form of an annular conductive layer symmetrical with respect to said axis, positioned adjacent, and symmetrically with respect to, opposite sides of said plane for creating on said opposite sides, and on said axis, a pair of symmetrically spaced point-foci with respect to said expanse.

2. The antenna of claim 1, wherein said foci are spaced by substantially one-half of said selected wavelength.

3. The antenna of claim 1 which further comprises conductive bidirectional director means located on axially opposite sides of said expanse for directing radiation bidirectionally between said expanse and said foci.

4. The antenna of claim 3, wherein said foci are spaced by substantially one-half of said selected wavelength.

5. A microwave antenna comprising
driven element means, having a central plane, coupleable to a source of microwave energy to be driven thereby, and adapted, when so driven, to radiate such energy simultaneously in opposite directions from said element means along a common axis which is normal to said plane, and
bidirectional focusing means, including electromagnetic/electrostatic shield means in the form of an annular conductive layer symmetrical with respect to said axis, positioned adjacent and on opposite sides of said element means for converging energy radiated thereby toward a pair of point-foci spaced on said opposite sides of said element means and located on said axis.

6. The antenna of claim 5, wherein said element means comprises a planar conductive ring.

7. The antenna of claim 5 which further includes bidirectional director means positioned adjacent said element means for directing radiation therefrom toward said foci.

8. The antenna of claim 7, wherein said element means and said director means are unitary.

9. The antenna of claim 7, wherein said driven element means has an axis of symmetry coincident with said common axis, and said driven element means and said director means, when viewed in a radial plane containing said axis of symmetry and on one side only of such axis in said radial plane, are disposed along a portion of a sinusoidal path.

10. The antenna of claim 7, wherein said element means comprises a planar conductive ring occupying said central plane, and said director means comprises annular conductive means disposed on axially opposite sides of the plane of said element means.

11. The antenna of claim 10, wherein each of said conductive means comprises a plurality of spaced, planar, conductive director rings arranged coaxially with said driven element means.

12. The antenna of claim 10 wherein, considering all of said rings, said driven ring has a larger nominal diameter than each of those of said director rings, and the nominal diameters of the latter become smaller progressing in both directions axially away from the plane of said driven ring.

13. The antenna of claim 12, wherein said driven ring has an axis of symmetry coincident with said common axis, and said driven ring and said director rings, when viewed in a radial plane containing said axis of symmetry and on one side only of such axis in said radial plane, are disposed along a portion of a sinusoidal path.

14. A bidirectional focusing microwave antenna for transmitting microwave radiation simultaneously in opposite directions at a selected wavelength along a common axis, said antenna comprising a first antenna element electrically coupleable to a source of microwave energy to be driven thereby for the purpose of radiating such energy, said first element taking the form of a planar endless conductive ring having a nominal circumference whose size is related in a predetermined mathematical ratio to said selected wavelength, and focusing means, including elecromagnetic/electrostatic shield means in the form of an annular conductive layer symmetrical with respect to said axis, disposed symmetrically and on opposite sides with respect to said element for converging radiation transmitted thereby in coaxially opposite directions toward a pair of spaced point-foci for the antenna, which foci are located at prechosen distances from said ring and on said common axis.

15. The antenna of claim 14, wherein said nominal circumference is substantially equal to said selected wavelength, 16. The antenna of claim 14, wherein said focusing means is constructed to place said foci at substantially equal distances on opposite sides of the plane of said ring.

17. The antenna of claim 16, wherein each of said distances substantially equals one-quarter of said selected wavelength.

18. The antenna of claim 14, wherein said focusing means takes the form of an elongated, somewhat donut-shaped housing coaxial with and surrounding said ring, the inside wall of said housing, when viewed in any radial plane containing the axis of symmetry of said ring, which axis is coincident with said common axis, and on one side only of such axis in such plane, curving along a portion of a generally sinusoidal path which is arranged symmetrically with respect to said ring.

19. The antenna of claim 18, wherein said generally sinusoidal path extends from opposite ends of said antenna and intersects the transmission axis of the antenna at the locations of said two foci.

20. The antenna of claim 18, wherein said ring is partially imbedded in said inside wall to a depth such that the location of its nominal circumference lies at all points in a path coextensive with said generally sinusoidal path.

21. The antenna of claim 18, wherein the wall thickness of said housing tapers, progressing axially in opposite directions from the plane of said ring, toward the opposite ends of the housing.

22. The antenna of claim 21, wherein said wall thickness of said housing, as measured radially in different axially displaced planes paralleling the central plane of said ring, is at all points a constant fraction of the inside diameters of the housing wall as measured, respectively in such displaced planes.

23. The antenna of claim 14 which further includes bidirectional director means positioned adjacent said first element for directing radiation therefrom toward said foci.

24. The antenna of claim 23, wherein said director means comprises annular conductive means disposed on axially opposite sides of the plane of said ring.

25. The antenna of claim 24, wherein each of said conductive means comprises a plurality of spaced planar conductive director rings arranged coaxially with said first-mentioned ring.

26. The antenna of claim 25, wherein all of said rings, when viewed in any radial plane containing the transmission axis of said antenna, which axis is coincident with said common axis, and on one side only of such axis in such plane, are disposed along a portion of a sinusoidal path.

27. A bidirectional, simultaneous-opposed-direction focusing transmission/reception antenna for electromagnetic radiation of a selected wavelength comprising means defining a pair of spaced radiation-effective points whose locations relative to one another are related to said selected wavelength, said points occupying a central plane in the antenna, and bidirectional focusing means, including electromagnetic/electrostatic shield means in the form of an annular conductive layer symmetrical with respect to said axis, positioned adjacent and on opposite sides of said central plane for creating a pair of spaced point-foci with respect to said points, said foci being located on said opposite sides of said central plane and along a common axis which is normal to said plane.

28. The antenna of claim 27, wherein said focusing means is disposed symmetrically with respect to said points, and produces locations for said foci which are each spaced substantially one-quarter of the distance of said selected wavelength from a line containing said points.

* * * * *